US008623637B2

(12) United States Patent
Ikeda

(10) Patent No.: US 8,623,637 B2
(45) Date of Patent: Jan. 7, 2014

(54) NUCLEIC ACID AMPLIFICATION APPARATUS AND THERMAL CYCLER

(75) Inventor: Ikumasa Ikeda, Miura-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 427 days.

(21) Appl. No.: 12/336,264

(22) Filed: Dec. 16, 2008

(65) Prior Publication Data

US 2009/0162929 A1 Jun. 25, 2009

(30) Foreign Application Priority Data

Dec. 21, 2007 (JP) ................................ 2007-330965

(51) Int. Cl.

*C12M 1/34* (2006.01)
*C12M 1/00* (2006.01)
*C12M 3/00* (2006.01)
*C12Q 1/68* (2006.01)

(52) U.S. Cl.

USPC .................... 435/287.2; 435/6.11; 435/288.5; 435/303.1

(58) Field of Classification Search

USPC ........................ 435/287.2, 288.5, 6.11, 303.1
See application file for complete search history.

(56) References Cited

U.S. PATENT DOCUMENTS

| | | | | |
|---|---|---|---|---|
| 5,720,923 | A | 2/1998 | Haff | |
| 6,174,675 | B1 * | 1/2001 | Chow et al. | 435/6 |
| 6,960,437 | B2 * | 11/2005 | Enzelberger et al. | 435/6 |
| 7,156,969 | B2 * | 1/2007 | Mehta et al. | 204/455 |
| 2005/0186585 | A1 * | 8/2005 | Juncosa et al. | 435/6 |
| 2006/0011478 | A1 * | 1/2006 | Fouillet et al. | 204/451 |

FOREIGN PATENT DOCUMENTS

| | | | |
|---|---|---|---|
| JP | 06-30776 | A | 2/1994 |
| JP | 07-075544 | A | 3/1995 |
| JP | 2001-521622 | T | 11/2001 |
| WO | WO98/45481 | | 10/1998 |

OTHER PUBLICATIONS

Martin U. Kopp, Andrew J. De Mello, Andreas Manz, "Chemical Amplification: Continuous-Flow PCR on a Chip", Science, vol. 280, May 15, 1998, pp. 1046-1048.

* cited by examiner

*Primary Examiner* — Nathan Bowers
*Assistant Examiner* — Gautam Prakash
(74) *Attorney, Agent, or Firm* — Canon U.S.A., Inc., IP Division

(57) ABSTRACT

A thermal cycler is provided that may be used as a nucleic acid amplification apparatus. The cycler has at least three temperature zones that can be set at different temperatures, the temperature zones including a first temperature zone, an intermediate zone, and a second temperature zone. The cycler has a channel including a plurality of forward subchannels and a plurality of backward subchannels, with the forward subchannels being different from the backward subchannels in terms of cross-sectional area in the intermediate zone. The channel is configured to continuously flow a fluid alternately through one of the forward subchannels and one of the backward subchannels, so that the fluid travels repeatedly between the first temperature zone and the second temperature zone via the intermediate zone, whereby the fluid is thermally cycled while the fluid flows through the channel.

6 Claims, 5 Drawing Sheets

NUCLEIC ACID AMPLIFICATION APPARATUS AND THERMAL CYCLER

BACKGROUND OF THE INVENTION

1. Field of the Invention

The present invention generally relates to a thermal cycler, such as for a nucleic acid amplification apparatus. Specifically, the present invention may relate to a nucleic acid amplification apparatus that thermally cycles a fluid containing nucleic acid, by causing the fluid to flow in a channel running through temperature zones set at different temperatures, thereby amplifying the nucleic acid.

2. Description of the Related Art

To efficiently duplicate and amplify a very small amount of template DNA, a polymerase chain reaction (PCR) method is commonly used. The PCR method achieves amplification of DNA of interest through repetition of a thermal cycle including the following steps (1) to (3). The step (1) is a denaturing step for thermally denaturing double-stranded DNA into single-stranded DNA, which functions as a template. The step (2) is an annealing step for annealing the template and primers that are complementary to the template. The step (3) is an extension step for synthesizing double-stranded DNA, by forming a DNA strand that is complementary to the template from the primers with a thermally stable DNA polymerase.

The steps are generally performed by controlling the temperatures and reaction times to which a reaction fluid is subjected, whereby an amplification reaction occurs in the reaction fluid. Typically, double-stranded DNA is thermally denatured into single-stranded DNA, which functions as a template, at a temperature of about 94° C. Primers are annealed to single-stranded DNA at a temperature of about 65° C. A DNA strand that is complementary to the template is synthesized with a DNA polymerase at a temperature of about 72° C.

An apparatus exists that automatically performs the PCR method by changing the temperature of a reaction fluid in an Eppendorf tube with a heater and a cooler. The reaction fluid contains template DNA, primers, deoxyribonucleoside triphosphate (dNTP), a DNA polymerase, and the like. The apparatus has wells formed in an aluminum block, and may control the temperature of the block, thereby controlling the temperature of the Eppendorf tubes inserted into the wells.

In the PCR method, thermal cycling may need to be performed under accurate control of temperature. However, when the PCR method is performed as the batch reaction described above, thermal fluctuation of the reaction system may considerably increase as the scale of the system increases. For this reason, the degree to which the scale of the system can be increased is generally restricted.

Japanese Patent Laid-Open Nos. 06-30776 and 07-075544 and Kopp M U; Mello A J; Manz A., Science, 1998, 280, 5366, pp 1046-1048 disclose a continuous flow PCR method with which it is claimed that thermal cycling can be performed under accurate control of temperature, and increasing the scale of the system can also be achieved. In the method, a reaction fluid containing a DNA polymerase, template DNA, primer DNA, dNTP, and the like, is thermally cycled by flowing the fluid through a channel running through a heated zone and a cooled zone, thereby performing the PCR.

FIG. 2 of PCT Japanese Translation Patent Publication No. 2001-521622 shows a PCR method in which a current is passed through a fluid flowing through a channel, thereby generating joule heat. The fluid has a temperature that depends on dissipation of heat from the channel. The fluid at a position in the channel also has a temperature that depends on the cross-sectional area of the channel at the position. The time for which the fluid flows at a certain temperature depends on the length of the channel. Thus, since the fluid at a position in the channel has a temperature that depends on the geometry of the channel and heat dissipation from the channel to the environment, the method may not provide sufficiently accurate temperature control.

The PCR method described in Kopp M U; Mello A J; Manz A., Science, 1998, 280, 5366, pp 1046-1048 is conducted with the following configuration. Three temperature zones are arranged in a plane in the order of 94° C., 73° C., and 55° C. zones. A portion of a channel in the 73° C. zone functions as a first intermediate portion in which a fluid rapidly flows from the 94° C. zone to the 55° C. zone. In contrast, another portion of the channel in the 73° C. zone functions as a second intermediate portion in which the fluid flows from the 55° C. zone to the 94° C. zone at a rate slower than that in the first intermediate portion, to provide sufficient time for extending DNA. To address these competing requirements, which include providing as short a passing time as possible as well as sufficient time for DNA extension in the respective intermediate portions at 73° C., the portions are provided with different channel lengths, whereby the fluid takes different amounts of time to pass through the portions. This configuration increases the length of the channel, thereby increasing flow resistance of the channel. To flow a PCR fluid through a long channel, pressure may be applied to the fluid. However, application of an excessively high negative pressure to a fluid can cause the fluid to boil, because the boiling point of the fluid is decreased under the pressure. Application of a high positive pressure to a fluid may require taking measures for preventing the fluid from leaking, which can increase the size of cartridges and the costs of producing such cartridges. A longer channel may also adsorb a larger portion of template DNA molecules, decreasing amplification yield. A longer channel may also require a larger plane area where the channel is to be arranged, and hence size reduction of an apparatus employing the PCR method may not be achieved.

SUMMARY OF THE INVENTION

According to one embodiment of the present invention, a nucleic acid amplification apparatus is provided that includes at least three temperature zones that can be set at different temperatures, the temperature zones including a first temperature zone, an intermediate zone, and a second temperature zone. The apparatus also has a channel including a plurality of forward subchannels and a plurality of backward subchannels, the channel being configured to continuously flow a fluid containing nucleic acid alternately through one of the forward subchannels and one of the backward subchannels, so that the fluid travels repeatedly between the first temperature zone and the second temperature zone via the intermediate zone, whereby the fluid is thermally cycled to achieve an amplification reaction of the nucleic acid while the fluid flows through the channel, the forward subchannels being different from the backward subchannels in terms of cross-sectional area in the intermediate zone.

According to another embodiment of present invention, a thermal cycler is provided that includes at least three temperature zones that can be set at different temperatures, the temperature zones including a first temperature zone, an intermediate zone, and a second temperature zone. The cycler also has a channel including a plurality of forward subchannels and a plurality of backward subchannels, the channel being configured to continuously flow a fluid alternately through one of the forward subchannels and one of the backward subchannels, so that the fluid travels repeatedly between the first temperature zone and the second temperature zone via the intermediate zone, whereby the fluid is thermally cycled while the fluid flows through the channel, the forward subchannels being different from the backward subchannels in terms of cross-sectional area in the intermediate zone.

Further features of the present invention will become apparent from the following description of exemplary embodiments with reference to the attached drawings.

DESCRIPTION OF THE EMBODIMENTS

Figures 1A, 1B, 1C:
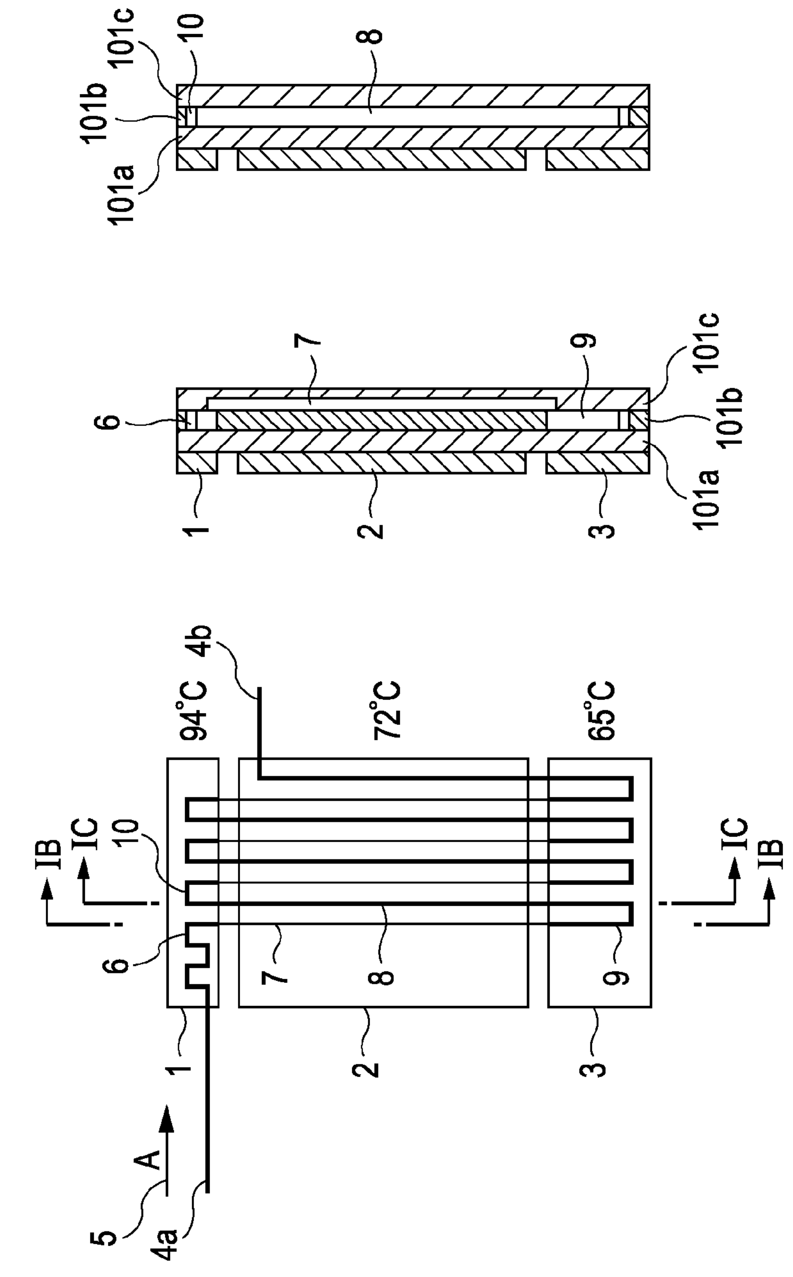
FIG. 1A is a partial schematic view of a channel of a nucleic acid amplification apparatus according to an embodiment of the present invention.
FIG. 1B is a cross section of the embodiment of the nucleic acid amplification apparatus of FIG. 1A taken along section line IB-IB of FIG. 1A.
FIG. 1C is a cross section of the embodiment of the nucleic acid amplification apparatus taken along section line IC-IC of FIG. 1A.

The inventors of the present invention have found that, in one version, the size of nuclear acid amplification apparatus can be reduced while also performing the amplification reaction relatively efficiently. In one version, this may be achieved by reducing the residence time of a reaction fluid flowing through a channel, and by increasing the cross-sectional area of at least one of a forward subchannel and a backward subchannel of one cycle, thereby increasing the cross-sectional area of at least one of forward subchannels and backward subchannels in a plurality of cycles.

In one version, in a system performing PCR at three temperatures, predetermined primers can be annealed to predetermined positions on templates by subjecting a fluid containing the primers and the templates to a temperature transition from a denaturing step (e.g., about 94° C.) to an annealing step (e.g., about 55° C.) in a reduced amount of time. A reduction in the time of such a temperature transition occurring in several tens of thermal cycles may provide a significant reduction in amplification time.

Examples of a fluid used in the present invention include a reaction fluid for a nucleic acid amplification reaction. Such a reaction fluid may contain at least nucleic acids that function as templates (hereafter referred to as templates), nucleic acids that function as primers (hereafter referred to as primers), a DNA polymerase, and deoxynucleoside triphosphate (dNTP), which serves as a material (substrate) for DNA synthesis.

In one embodiment according to the present invention, such a fluid may be flowed through a channel of a nucleic acid amplification apparatus, whereby the fluid is thermally cycled. In the thermal cycling, the following three steps may be repeated: denaturing of templates, annealing of the denatured templates and primers, and extension of nucleic acid sequences with an enzyme for synthesizing the nucleic acid sequences.

In one version, such thermal cycling is performed in a nucleic acid amplification apparatus having at least three temperature zones that can be set at different temperatures, the temperature zones including a first temperature zone, an intermediate zone, and a second temperature zone. The apparatus may also have a channel that comprises a plurality of forward subchannels and a plurality of backward subchannels, the channel being configured to continuously flow a fluid containing nucleic acid alternately through one of the forward subchannels and one of the backward subchannels, so that the fluid travels repeatedly between the first temperature zone and the second temperature zone via the intermediate zone, whereby the fluid may be thermally cycled to achieve an amplification reaction of the nucleic acid while the fluid flows through the channel.

In accordance with one embodiment, the amplification reaction includes a denaturing reaction, an annealing reaction, and an extension reaction. In one version, the three temperature zones respectively correspond to a denaturing zone where the denaturing reaction is performed, an annealing zone where the annealing reaction is performed, and an extension zone where the extension reaction is performed.

According to one aspect of the present invention, the temperature zones can include an intermediate zone, a first temperature zone, and a second temperature zone. In one version, the channel may run back and forth between the first temperature zone and the second temperature zone via the intermediate zone.

That is, in one version, the channel includes a plurality of forward subchannels and a plurality of backward subchannels running between the first temperature zone and the second temperature zone. For example, the forward subchannels may extend from the first temperature zone to the second temperature zone via the intermediate zone, while the backward subchannels extend from the second temperature zone to the first temperature zone via the intermediate zone.

Although the three temperature zones may be arranged in any configuration, in one embodiment they may be arranged side-by-side in a row. In particular, in one version, the intermediate zone may be disposed between the first temperature zone and the second temperature zone such that the three temperature zones are in line with one another. Examples of a combination of the intermediate zone, the first temperature zone, and the second temperature zone are described below.

(1) In one embodiment, the extension reaction is performed in the intermediate zone. According to this embodiment the denaturing reaction is performed in one of the first temperature zone and the second temperature zone, while the annealing reaction is performed in the other one of the first temperature zone and the second temperature zone.

(2) In another embodiment, the annealing reaction is performed in the intermediate zone. According to this embodiment the denaturing reaction is performed in one of the first temperature zone and the second temperature zone, while the extension reaction is performed in the other one of the first temperature zone and the second temperature zone.

(3) In yet another embodiment, the denaturing reaction is performed in the intermediate zone. According to this embodiment, the annealing reaction is performed in one of the first temperature zone and the second temperature zone, while the extension reaction is performed in the other one of the first temperature zone and the second temperature zone.

In one version, the channel through which the fluid is flowed may have forward subchannels that are different from the backward subchannels in terms of cross-sectional area in the intermediate zone.

For example, in the embodiment of case (1), the subchannels may have different cross-sectional areas in the extension reaction zone, depending on the flow direction of a fluid. In this embodiment, the fluid flows through one of forward subchannels and backward subchannels from the denaturing zone to the annealing zone, whereas the fluid flows through the other one of the forward subchannels and backward subchannels in the reverse direction. The term "denaturing templates" as used herein refers to melting double-stranded nucleic acid into a single-stranded form.

Such a configuration including subchannels with different cross-sectional areas can provide advantages. For example, when a fluid flows from a subchannel with a smaller cross-sectional area into another subchannel with a larger cross-sectional area, mixing within the fluid tends to occur in the subchannel with the larger cross-sectional area. This can improve the efficiency of amplification by improving the probability of contact between substances within a certain distance in relatively narrow channels.

In one embodiment, in the denaturing zone, the channel may be equipped with an external temperature controller, so that a reaction fluid flowing through the channel can be heated to a temperature equivalent to a melting point or more of a nucleic acid. In another embodiment, in the annealing zone, the channel may be equipped with an external temperature controller so that a reaction fluid flowing through the channel can be controlled to have a temperature equivalent to a melting point or less of the nucleic acid. Such temperature controllers may be any controllers, for example as long as they can control temperatures in the intended zones. Such temperature controllers may include, for example, resistance heaters and Peltier devices.

Examples of a nucleic acid synthetic enzyme suitable for the present invention can include commercially available enzymes that can be used for amplifying nucleic acid. Specific examples of such enzymes may include, but are not limited to, DNA polymerase, ligase, reverse transcriptase, and RNA polymerase. These enzymes may also be used in combination with each other.

In one version, the channel may be formed of a material having a relatively high thermal conductivity. The channel may also be relatively stable in a temperature range suitable for performing PCR, and may be resistant to corrosion by electrolytic solutions and organic solvents. The channel may also exhibit relatively low adsorption of nucleic acids and proteins. Examples of a material resistant to heat and corrosion may include, but are not limited to, glass, quartz, silicon, and various plastics. In one version, a surface (e.g., an interior wall that comes in contact with a reaction fluid) of the channel may be coated with a compound exhibiting low adsorption of nucleic acids and proteins, such as for example at least one of polyethylene and polypropylene. In another version, adsorption of nucleic acids and proteins on the surface may be reduced by introducing molecules having many hydrophilic functional groups to the surface, such as for example by introducing polyethylene glycol (PEG) to the surface through covalent bonding or the like.

In one embodiment, to denature templates, anneal denatured templates and primers, and synthesize nucleic acid in a channel efficiently in an apparatus according to the present invention, conditions such as the flow rate of the reaction fluid and the cross-sectional areas and length of the channel may be adjusted. These conditions may be determined in accordance with parameters such as at least one of the lengths of the templates, the lengths of the nucleic acid sequences to be synthesized, the reaction rate of a nucleic acid synthetic enzyme, and the like.

The present invention is specifically described below with reference to embodiments. However, the specific embodiments described herein are not intended to restrict the scope of the present invention.

Hereinafter, a nucleic acid amplification apparatus according to a first embodiment is described with reference to the drawings. Like element numerals are used to describe like elements and avoid redundant description. In FIGS. 1A, 3, 4, 5, and 6, the width of each channel portion represents, i.e. is proportional to, its cross-sectional area.

Figure 2:
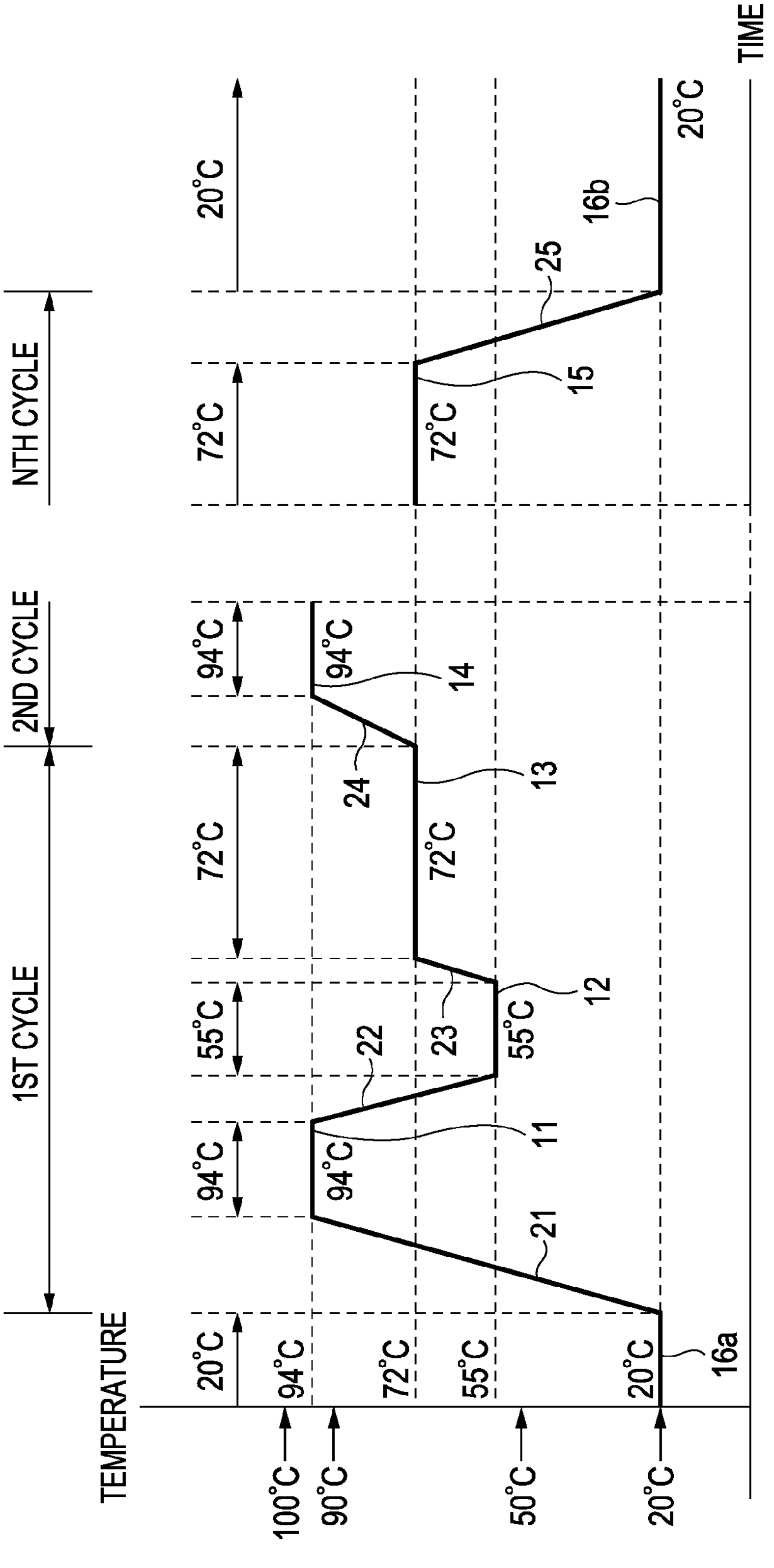
FIG. 2 shows an example of temperature transitions over time for a fluid flowing through a channel of a nucleic acid amplification apparatus according to an embodiment of the present invention.

FIG. 2 shows thermal cycles of PCR amplification according to an embodiment of the present invention. The horizontal axis of the graph represents time while the vertical axis represents temperature. Reference numerals **16*a* and 16*b* denote states at about room temperature. Reference numeral 11 denotes a denaturing step. Reference numeral 12 denotes an annealing step. Reference numeral 13 denotes an extension step. The amplification is achieved by repeating the denaturing step, annealing step, and the extension step. After a last extension step 15 is complete, the reaction fluid is cooled to room temperature 16*b* to end the thermal cycles. The initial denaturing step 11 may be generally performed for a longer period than later denaturing steps. For example, a longer initial denaturing step 11 may be provided when hot start PCR is performed. Reference numerals 21, 22, 23, and 24 denote temperature transitions among room temperature (16*a*), denaturing temperature (11), annealing temperature (12), extension temperature (13), and denaturing temperature (14). Reference numeral 25 denotes a temperature transition between extension temperature (15) and room temperature (16*b***).

FIG. 1 shows a nucleic acid amplification apparatus according to a first embodiment of the present invention. Reference numerals 4 denote channel portions. Reference numerals 1, 2, and 3 denote temperature zones controlled to respective certain temperatures. In the embodiment as shown, the temperature zone 1 is set at a denaturing temperature for denaturing double-stranded nucleic acid into a single-stranded form.

Also in the embodiment as shown, the temperature zone 2, which serves as an intermediate zone, is set at an extension temperature for extending annealed double-stranded sequences. The temperature zone 3 is set at an annealing temperature for annealing templates and primers. A fluid flows through a channel portion **4*a* in the direction A denoted by reference numeral 5**.

According to this embodiment, the fluid flows from the channel portion **4*a*, in the following order, to a channel portion 6 in the denaturing temperature zone 1, a channel portion 7 in the extension temperature zone 2, a channel portion 9 in the annealing temperature zone 3, and back to a channel portion 8 in the extension temperature zone 2. Finally, the fluid arrives at channel portion 4*b* through a channel portion 10**.

In one version, the fluid in the channel portion 7 in the extension temperature zone 2, which functions as an intermediate zone in FIG. 1, may flow to the annealing temperature zone 3 as fast as possible. To perform amplification, certain primers may be bound to templates at predetermined positions in the annealing step. Thus, in one version, the entirety of a fluid in the annealing step may be made to reach a predetermined temperature relatively precisely and rapidly. In one embodiment, this may be achieved by providing a channel portion having a relatively small cross-sectional area as the channel portion 7. In contrast, a fluid may be made to take a certain amount of time to pass through the channel portion 8. In one embodiment, this may be achieved by providing a channel portion having a relatively large cross-sectional area as the channel portion 8.

Referring to FIGS. 1B and 1C, in one embodiment a cartridge comprises three layers of members 101*a*, 101*b*, and 101*c*. In one version, the channel portion 8 with the larger cross-sectional area may be formed by hollowing the member 101*b* out by an amount corresponding to its entire thickness. In another version, the channel portion 7 with the smaller cross-sectional area may be formed by removing a part of the member 101*c*. The channel portions running through the member 101*b* may be sealed with the member 101*a*. In this way, the cross-sectional areas of the channel portions may be adjusted in the thickness direction of the members, and hence, a plurality of subchannels can be arranged relatively densely in the horizontal plane of the cartridge. Such a configuration may be suitable to provide for decreased size of the nucleic acid amplification apparatus.

Figure 3:
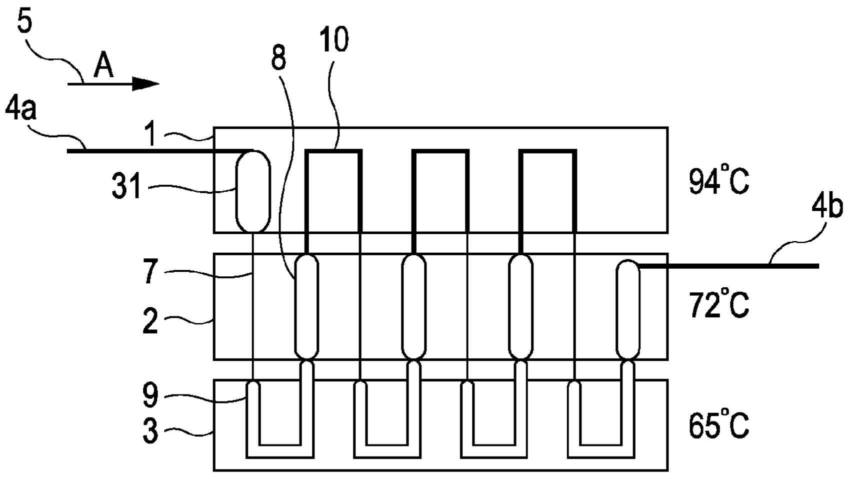
FIG. 3 shows a nucleic acid amplification apparatus according to another embodiment of the present invention.

Referring to another configuration as shown in the embodiment of FIG. 3, to keep a fluid for a longer period of time at the denaturing temperature in the first cycle, a channel portion 31 in the denaturing temperature zone may have a larger cross-sectional area than the other channel portions in the denaturing temperature zone in the following cycles. The same numerals in FIG. 3 represent the same elements as those in FIG. 1.

As described above, in the first embodiment the channel portions 7 and 8 in the extension temperature zone 2 may have different cross-sectional areas. The channel portions 7 and 8 may also have different lengths. For example, the channel portion 8 may have a larger length, thereby increasing the residence time of the fluid in the extension temperature zone 2.

Figure 4:
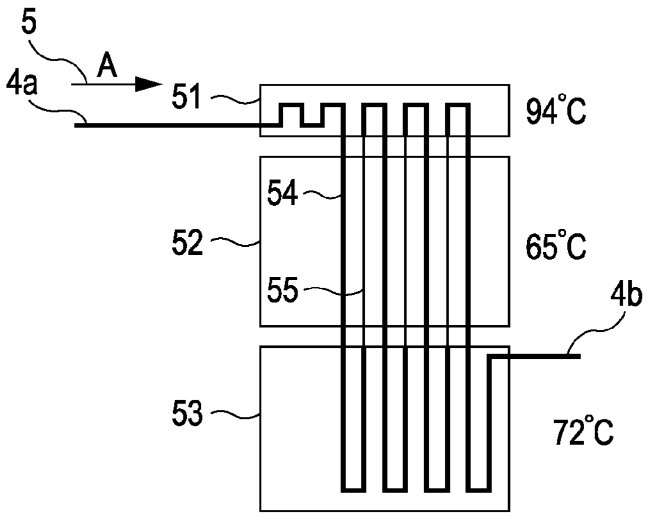
FIG. 4 shows a nucleic acid amplification apparatus according to still another embodiment of the present invention.

FIG. 4 shows a nucleic acid amplification apparatus according to a second embodiment of the present invention. The configuration of FIG. 4 has, in sequence, a denaturing temperature zone 51, an annealing temperature zone 52, and an extension temperature zone 53 whereas, by comparison, the configuration of FIG. 1 has, in sequence, the denaturing temperature zone 1, the extension temperature zone 2, and the annealing temperature zone 3. That is, the positions of the annealing temperature zone 52 and the extension temperature zone 53 are exchanged between the configurations shown in FIG. 4 and FIG. 1.

In the configuration of FIG. 4, where the denaturing temperature zone 51 is adjacent to the annealing temperature zone 52, a PCR fluid flowing through a channel is moved relatively rapidly from the denaturing step to the annealing step, achieving fairly rapid temperature transition of the fluid. Since the annealing temperature zone 52 is adjacent to the extension temperature zone 53, temperature transition of the fluid between the zones can be also achieved relatively smoothly. However, when the fluid is moved from the extension temperature zone 53 to the denaturing temperature zone 51, the fluid may be made to pass through the annealing temperature zone 52 relatively rapidly. For example, this may be achieved by providing a channel portion 55 with a relatively small cross-sectional area. Thus, although the fluid passes through the annealing temperature zone 52 from the extension step to the denaturing step in the configuration as shown in FIG. 4, this passing may not considerably affect the nucleic acid sequences in the fluid, because the sequences have already been at least partially and even fully extended in the extension step. The extension step may also generally take more time than the annealing step. In one embodiment, a temperature zone positioned at an end of a row of temperature zones, such as for example the extension temperature zone 53, may have relatively long channel portions because the channel portions turn around before passing back into the adjacent temperature zone. Thus, the configuration of FIG. 4 may be advantageous in that longer channel portions can be provided for the extension step, which may provide a relatively longer residence time of the fluid.

Figure 5:
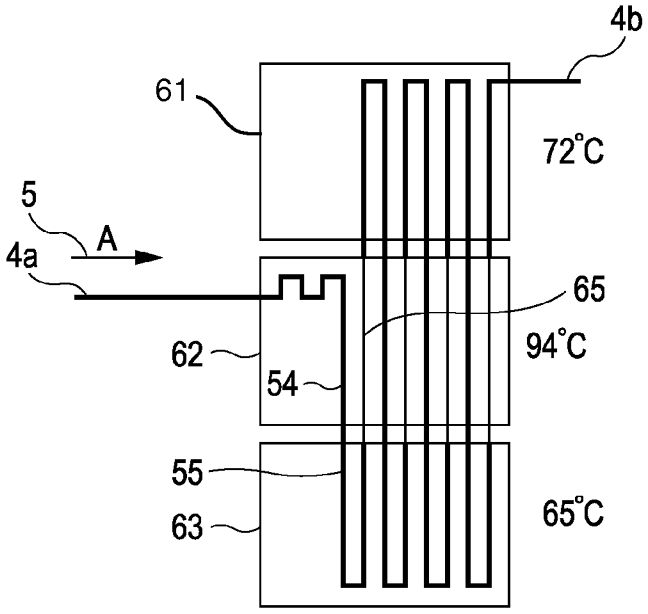
FIG. 5 shows a nucleic acid amplification apparatus according to a further embodiment of the present invention.

FIG. 5 shows a nucleic acid amplification apparatus according to a third embodiment of the present invention. The configuration of FIG. 5 has, in sequence, an extension temperature zone 61, a denaturing temperature zone 62, and an annealing temperature zone 63, whereas by comparison the configuration of FIG. 1 has, in sequence, the denaturing temperature zone 1, the extension temperature zone 2, and the annealing temperature zone 3. That is, the positions of the extension temperature zone 61 and the denaturing temperature zone 62 are exchanged between the configurations of FIG. 5 and FIG. 1.

In the configuration as shown in the embodiment of FIG. 5, where the denaturing temperature zone 62 is adjacent to the annealing temperature zone 63, a PCR fluid flowing through a channel is moved relatively rapidly from the denaturing step to the annealing step, achieving a fairly rapid temperature transition of the fluid. When the PCR fluid is moved from the annealing step to the extension step in the configuration of FIG. 5, the fluid passes through the denaturing temperature zone 62. This may cause template-primer complexes that have been formed in the annealing step to at least partially separate. For this reason, in one version the occurrence of the denaturing reaction may be reduced by passing the fluid through a channel portion 65 in the denaturing temperature zone 62 at a relatively high rate, for example as fast as possible. In one embodiment, this may be achieved by providing a channel portion with a relatively small cross-sectional area as the channel portion 65 than channel portion 54, thereby increasing the flow rate of the fluid through the channel portion 65 and decreasing the time period for passing through the denaturing temperature zone 62. Among the denaturing step, the annealing step, and the extension step in a general thermal cycle, the extension step and the annealing step may take more time than the denaturing step, and may even take much more time than the denaturing step; and the extension step may take more time than the annealing step. In one embodiment, a temperature zone positioned at an end of a row of temperature zones, such as for example the extension temperature zone 61 and/or the annealing temperature zone 63, may have relatively long channel portions because the channel portions turn around before passing back into the adjacent temperature zone. The configuration of FIG. 5 may be advantageous in that temperature zones for the extension step and the annealing step, which may require a relatively longer residence time of the fluid, can be positioned at the ends of the row of the temperature zones.

Figure 6:
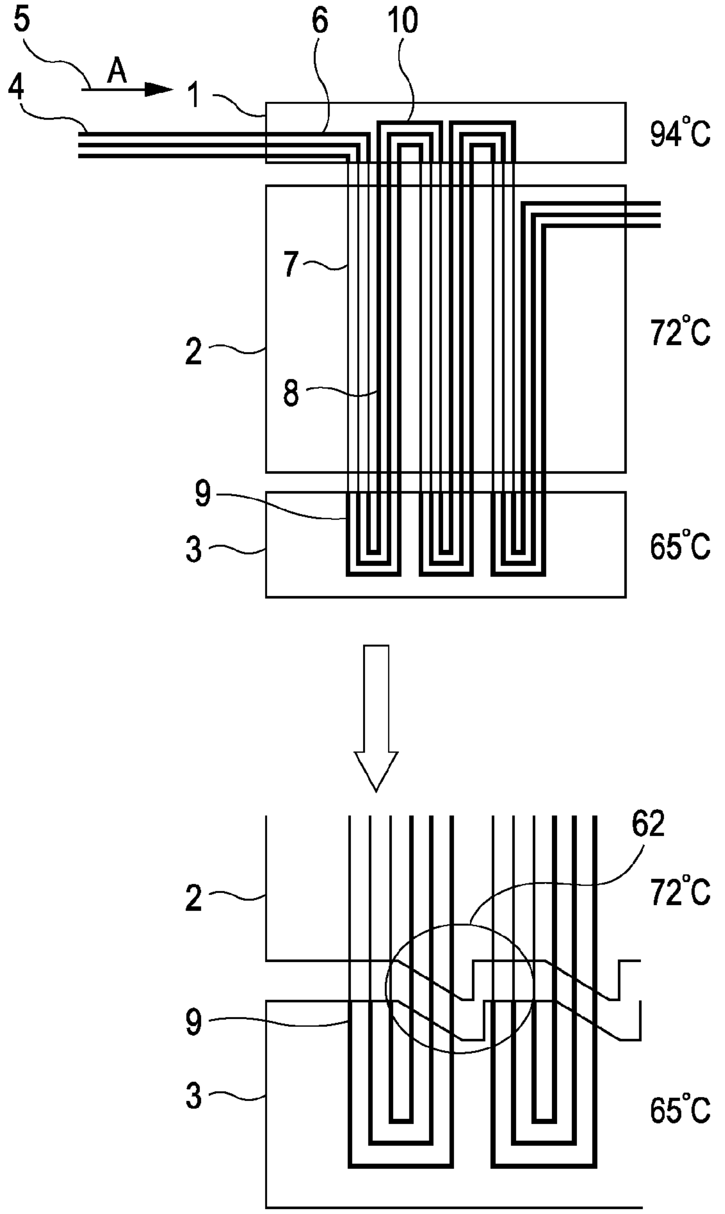
FIG. 6 shows a nucleic acid amplification apparatus having a plurality of channels according to an embodiment of the present invention.

FIG. 6 shows a fourth embodiment where a plurality of PCR amplifications are simultaneously performed with a cartridge having a plurality of channels. The fourth embodiment is different from the first embodiment as shown in FIG. 1 in that three channels are used. The channels are arranged not to overlap one another in the fourth embodiment as shown in FIG. 6, but the present invention is not intended to be restricted thereto. Since channel portions of the channels are heated in each temperature zone over which substantially the same temperature is maintained, temperature variation among the channel portions can be reduced. The configuration of FIG. 6 can also be designed so that the channels have the same total length. Such a configuration may be advantageous. In one version, to make the fluids in the channels have substantially the same residence time for each step, the temperature zones may have shapes such as those denoted by reference numeral 62 in a partial enlarged view of an area denoted by reference numeral 61.

Alternatively, in one embodiment, another configuration having a plurality of channels may be achieved by simply arranging the channel of FIG. 1 horizontally.

Alternatively, in yet another embodiment, another configuration having a plurality of channels can be formed with a cartridge having multiple layers in its thickness direction.

Although the present invention has been described with reference to thermal cycles for nucleic acid amplification reactions, it should be understood that the present invention is not intended to be restricted thereto. For example, the embodiments in accordance with the present invention may also be applicable to systems conducting other reactions with thermal cycles.

In the first embodiment, the cross-sectional area of a channel portion is adjusted by changing its depth. However, the present invention is not intended to be restricted thereto. The cross-sectional area of a channel portion can be changed, for example, by any one of the following techniques: (1) changing the width of the channel portion; (2) changing the depth of the channel portion; and (3) changing both the width and the depth of the channel portion.

The embodiments of the present invention described above may provide a nucleic acid amplification apparatus that permits size reduction of the apparatus, and that performs an amplification reaction relatively efficiently. The above-described embodiments of the present invention may also provide a cartridge-type nucleic acid amplification apparatus that facilitates isolation and purification of amplified nucleic acid, and that permits size reduction of the apparatus.

For example, according to the above-described embodiments of the present invention, the time for a thermal cycle in which a fluid travels back and forth among three temperature zones may be adjusted by changing the cross-sectional area of a channel, the cross-sectional area being proportional to and defining the residence time of the fluid. This may also enable considerable reduction in the plane area for arranging the channel.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-330965 filed Dec. 21, 2007, which is hereby incorporated by reference herein in its entirety.

What is claimed is:

1. A nucleic acid amplification apparatus comprising:

at least three temperature zones that can be set at different temperatures, the temperature zones including a first temperature zone, an intermediate zone, and a second temperature zone; and a plurality of channels each including a plurality of forward subchannels and a plurality of backward subchannels, the channel being configured to continuously flow a fluid containing nucleic acid alternately through one of the forward subchannels and one of the backward subchannels, so that the fluid travels repeatedly between the first temperature zone and the second temperature zone via the intermediate zone, whereby the fluid is thermally cycled to achieve an amplification reaction of the nucleic acid while the fluid flows through the channel, the forward subchannels being different from the backward subchannels in terms of cross-sectional area in the intermediate zone such that a residence time of a portion of the fluid in the forward subchannels in the intermediate zone is different than a residence time of a portion of the fluid in the backward subchannels in the intermediate zone;

a plurality of subchannels each connecting the forward subchannel and the backward subchannel, the plurality of subchannels being arranged such that a residence time of a portion of the fluid in each subchannel is the same in the first temperature zone, and such that a residence time of a portion of the fluid in each subchannel is the same in the second temperature zone; and a plurality of subchannels each connecting to one of the forward subchannels for conducting fluid to each of the channels, the plurality of subchannels being arranged parallel to each other.

2. The nucleic acid amplification apparatus according to claim 1, wherein the amplification reaction includes a denaturing reaction, an annealing reaction, and an extension reaction; and wherein the extension reaction is performed in the intermediate zone, the denaturing reaction is performed in either the first temperature zone or the second temperature zone, and the annealing reaction is performed in whichever of the first temperature zone or the second temperature zone that the denaturing reaction is not performed in; and further wherein the channel has channel portions that extend across the intermediate zone, the channel portions through which the fluid flows from the zone where the denaturing reaction is performed to the zone where the annealing reaction is performed having a smaller cross-sectional area than the channel portions through which the fluid flows from the zone where the annealing reaction is performed to the zone where the denaturing reaction is performed.

3. The nucleic acid amplification apparatus according to claim 1, wherein the amplification reaction includes a denaturing reaction, an annealing reaction, and an extension reaction; and wherein the annealing reaction is performed in the intermediate zone, the denaturing reaction is performed in either the first temperature zone or the second temperature zone, and the extension reaction is performed in whichever of the first temperature zone or the second temperature zone that the denaturing reaction is not performed in; and further wherein the channel has channel portions that extend across the intermediate zone, the channel portions through which the fluid flows from the zone where the extension reaction is performed to the zone where the denaturing reaction is performed having a smaller cross-sectional area than the channel portions through which the fluid flows from the zone where the denaturing reaction is performed to the zone where the extension reaction is performed.

4. The nucleic acid amplification apparatus according to claim 1, wherein the amplification reaction includes a denaturing reaction, an annealing reaction, and an extension reaction; and wherein the denaturing reaction is performed in the intermediate zone, the annealing reaction is performed in either the first temperature zone or the second temperature zone, and the extension reaction is performed in whichever of the first temperature zone or the second temperature zone that the denaturing zone is not performed in; and further wherein the channel has channel portions that extend across the intermediate zone, the channel portions through which the fluid flows from the zone where the annealing reaction is performed to the zone where the extension reaction is performed having a smaller cross-sectional area than the channel portions through which the fluid flows from the zone where the extension reaction is performed to the zone where the annealing reaction is performed.

5. The nucleic acid amplification apparatus according to claim 1, wherein the plurality of forward subchannels are adjacent to each other and the plurality of backward subchannels are adjacent to each other.

6. A thermal cycler comprising:

at least three temperature zones that can be set at different temperatures, the temperature zones including a first temperature zone, an intermediate zone, and a second temperature zone; and a plurality of channels each including a plurality of forward subchannels and a plurality of backward subchannels, the channel being configured to continuously flow a fluid alternately through one of the forward subchannels and one of the backward subchannels, so that the fluid travels repeatedly between the first temperature zone and the second temperature zone via the intermediate zone, whereby the fluid is thermally cycled while the fluid flows through the channel, the forward subchannels being different from the backward subchannels in terms of cross-sectional area in the intermediate zone such that a residence time of a portion of the fluid in the forward subchannels in the intermediate zone is different than a residence time of a portion of the fluid in the backward subchannels in the intermediate zone;

a plurality of subchannels each connecting the forward subchannel and the backward subchannel, the plurality of subchannels being arranged such that a residence time of a portion of the fluid in each subchannel is the same in the first temperature zone, and such that a residence time of a portion of the fluid in each subchannel is the same in the second temperature zone; and a plurality of subchannels each connecting to one of the forward subchannels for conducting fluid to each of the channels, the plurality of subchannels being arranged parallel to each other.

* * * * *